United States Patent [19]
MacLean

[11] Patent Number: 5,735,873
[45] Date of Patent: Apr. 7, 1998

[54] SURGICAL TOOL HANDLE

[76] Inventor: David S. MacLean, 34180 Lakeside Dr., Grays Lake, Ill. 60030

[21] Appl. No.: 769,426

[22] Filed: Dec. 19, 1996

[51] Int. Cl.$^6$ ............................................. A61B 17/00
[52] U.S. Cl. ................................... 606/205; 128/751
[58] Field of Search ........................... 606/51, 52, 170, 606/174, 205–210; 128/750–755; 81/415

[56] References Cited

U.S. PATENT DOCUMENTS

| | | | |
|---|---|---|---|
| 4,338,317 | 7/1982 | Hasson et al. | |
| 4,763,669 | 8/1988 | Jaeger | |
| 5,089,000 | 2/1992 | Agee | |
| 5,286,255 | 2/1994 | Weber | |
| 5,368,605 | 11/1994 | Miller, Jr. | 606/207 |
| 5,370,658 | 12/1994 | Scheller et al. | 606/174 |
| 5,409,478 | 4/1995 | Gerry et al. | |
| 5,439,461 | 8/1995 | Storz | 606/174 |
| 5,454,827 | 10/1995 | Aust et al. | |
| 5,470,328 | 11/1995 | Furnish et al. | 606/208 |
| 5,498,256 | 3/1996 | Furnish | 606/208 |
| 5,501,698 | 3/1996 | Roth et al. | 606/174 |

*Primary Examiner*—Michael Buiz
*Assistant Examiner*—William W. Lewis
*Attorney, Agent, or Firm*—Brinks Hofer Gilson & Lione

[57] ABSTRACT

A surgical tool includes a shaft having a distal end on which is mounted fixed and movable jaws. The movable jaw is positioned by a control rod which extends into a handle. The handle includes a rod actuator that is pivotably mounted in the handle and is coupled to the control rod such that pivoting movement of the actuator causes a control rod to translate. The handle includes a ratchet pawl that is coupled to the rod actuator, and the ratchet pawl is coupled to a ratchet actuator that is mounted in the handle and positioned to contact the palm of the user when the user grasps the handle and places a thumb on the rod actuator. Axial movement of the rod actuator can be used to move the ratchet pawl past a detent mechanism, to release the ratchet mechanism, or to lock the rod actuator in a predetermined position to facilitate installation and removal of the control rod. The user can apply pressure to the ratchet actuator with the palm to momentarily release the ratchet, or to move the ratchet pawl to an off position, in which it is held by the detent mechanism.

24 Claims, 7 Drawing Sheets

SURGICAL TOOL HANDLE

BACKGROUND OF THE INVENTION

This invention relates to handles for surgical tools, and in particular to an improved, ergonomic handle that is easily used and controlled.

In the past, a variety of handles for surgical tools such as forceps have been proposed. See for example Furnish U.S. Pat. No. 5,498,256 and Weber U.S. Pat. No. 5,286,255. Both of these patents disclose surgical tools of the type having a shaft, a movable element such as a forceps jaw mounted to the shaft, a handle mounted to the shaft, and a control rod coupled to the movable element and extending into the handle. The handle disclosed in the Furnish patent utilizes a button operated by the forefinger of the user to control operation of a ratchet pawl. The Weber patent discloses a surgical forceps with a scissors-like cutting tool on the distal end.

In spite of the prior art designs described above, a need presently exists for an improved surgical tool handle with improved operating and control characteristics.

SUMMARY OF THE INVENTION

The surgical tool handle described below incorporates a number of advances over the surgical tool handles described above. Though these advances are preferably used in combination, it should be understood that individual ones of these advances can be used separately from one another.

The advances included in the preferred embodiment described below include the following:

The handle includes a ratchet pawl which is controlled by a ratchet actuator positioned to contact the palm of a user when the user grasps the handle. This arrangement provides convenient and effective control of the pawl, without requiring the user to shift his or her grip on the handle.

The handle includes a pivotable rod actuator that is used to control the movable element of the surgical tool. This rod actuator includes a body and a ratchet control element. Pivoting forces on the ratchet control element operate the surgical tool in the conventional manner, and axial forces on the ratchet control element release the ratchet pawl.

The ratchet control element, when moved axially with respect to the handle, can be used to reset the pawl from an off position, in which it is held by a detent mechanism.

A portion of the rod actuator can be moved axially with respect to the body of the rod actuator into a recess formed in the handle in order to lock the rod actuator in the housing at a selected pivotal orientation to facilitate installation of the control rod in the body.

The handle includes a removably mounted finger engaging element that can be rotated to any of a number of positions in order to adjust the handle to the preferences of the user.

The rod actuator utilizes a preferred geometry to provide a stop surface for the control rod to provide repeatable performance, and to provide an increased mechanical advantage to the user as the jaws approach the fully closed position.

The handle includes a spring that biases the rod against the rod actuator to reduce or eliminate play therebetween.

These and other features of the preferred embodiment described below will be best understood by reference to the following detailed description, taken in conjunction with the accompanying drawings.

DETAILED DESCRIPTION OF THE PRESENTLY PREFERRED EMBODIMENTS

Figures 1, 2:
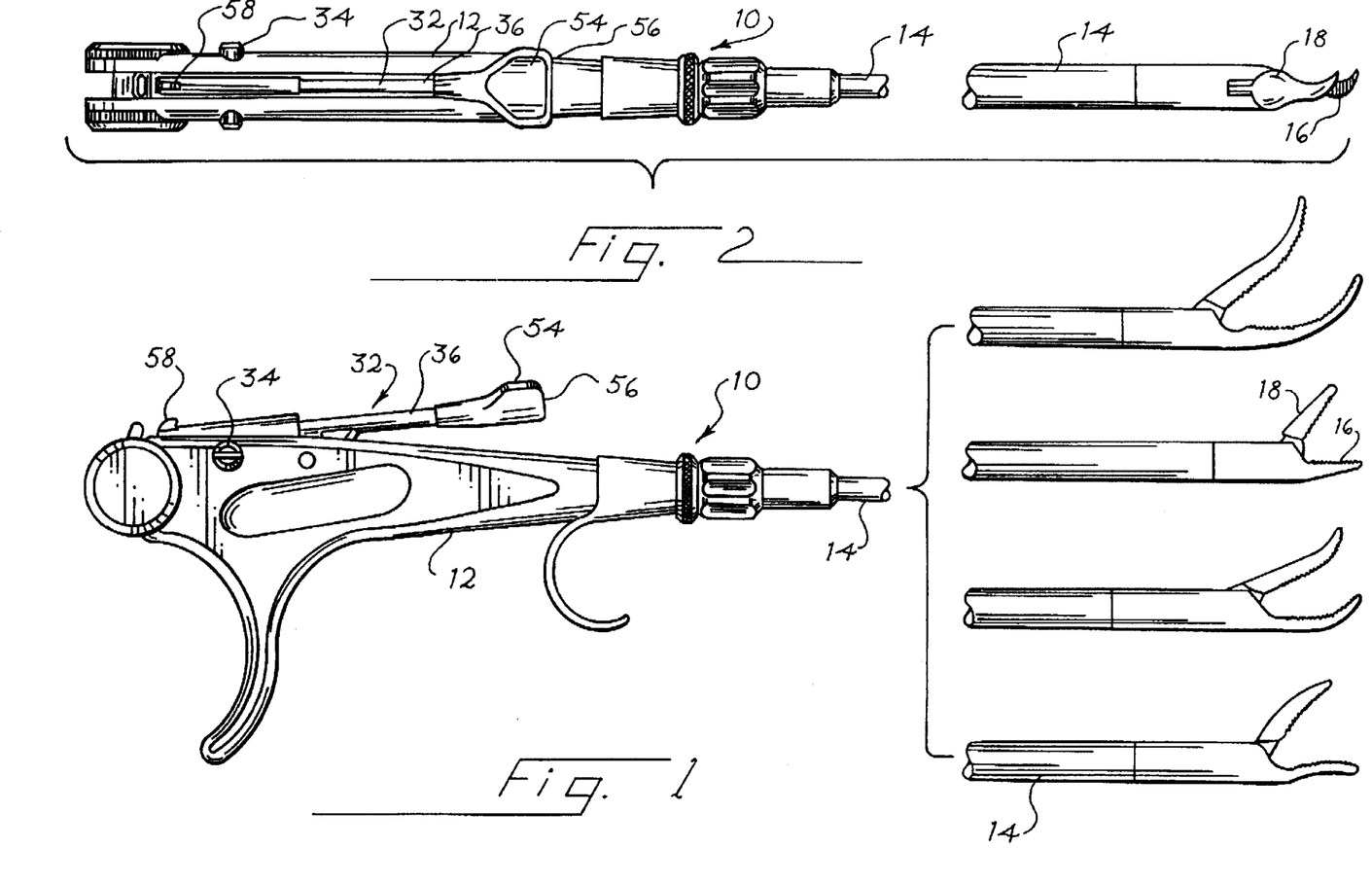
FIGS. 1 and 2 are side and top views, respectively, of a surgical tool handle which incorporates preferred embodiments of the present invention.

Turning now to the drawings, FIGS. 1 and 2 provide overall views of a surgical tool 10 that incorporates presently preferred embodiments of the present invention. The tool 10 includes a handle 12 that is removably connected to a shaft 14. The shaft 14 supports at its distal end a fixed jaw 16 and a movable jaw 18. The movable jaw 18 is mounted for pivoting movement, and the jaws 16, 18 can take any desired form. For example, the jaws 16, 18 can be shaped as forceps jaws as shown in FIG. 1. Alternately the jaws 16, 18 can be shaped as cutting tools. In FIGS. 1 and 2, the right side of the drawings are shown at an enlarged scale to show the jaws 16, 18 more clearly.

Figure 3:
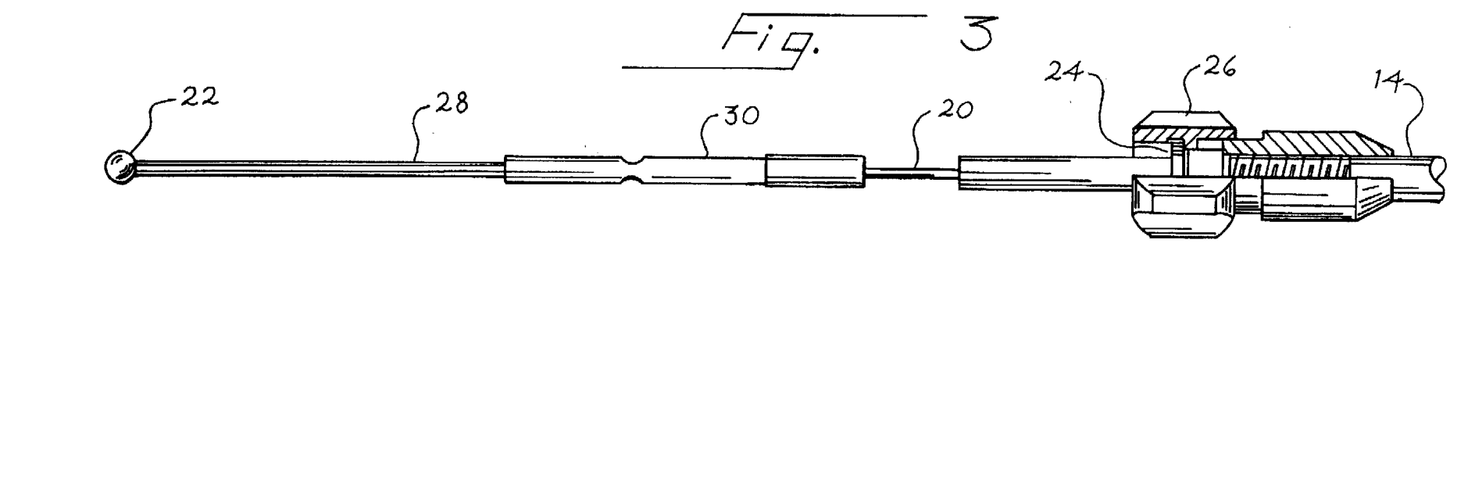
FIG. 3 is a side view in partial cut-away at an enlarged scale showing portions of a control rod and a shaft of the embodiment of FIGS. 1 and 2.

The movable jaw 18 is connected to a control rod 20 (FIG. 3), which terminates at its proximal end in a spherical end portion 22. As shown in FIG. 3, the shaft 14 supports a flange 24 and a threaded barrel 26. The threaded barrel 26 bears on the flange 24 to removably mount the shaft 14 to the handle 12. In this embodiment the spherical end portion 22 is integrally formed with a rod 28, which is connected to the remainder of the control rod 20 by a sleeve 30. The effective length of the control rod 20 can be calibrated precisely by establishing a fixed distance between the flange 24 and the end portion 22 (with the movable jaw 18 in a known position), and then immobilizing the sleeve 30 with respect to the control rod 20 and the rod 28, as for example by welding or brazing.

Returning to FIGS. 1 and 2, the handle 12 pivotably supports a rod actuator 32 for pivoting movement about a pivot axis 34. As described in detail below, pivotal movement of the rod actuator 32 results in translational movement of the control rod 20 and articulation of the movable jaw 18.

Figure 4:
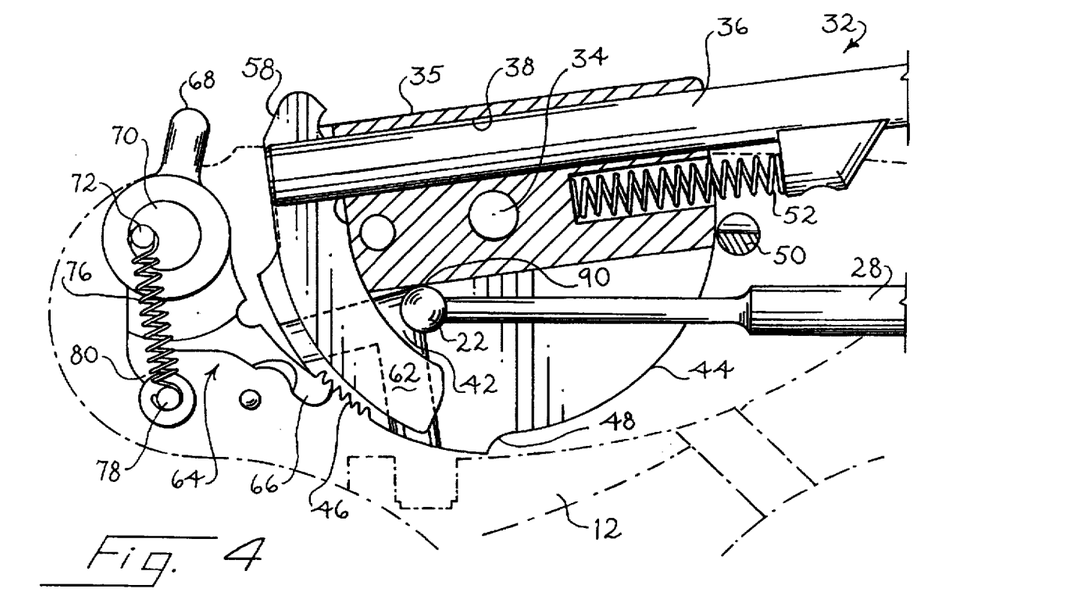
FIG. 4 is a partial cross-sectional view showing selected components of the embodiment of FIGS. 1 and 2.

Turning now to FIG. 4, the rod actuator 32 includes a body 35 and a ratchet control element 36. The body 35 defines a bore 38 sized to slidably receive the ratchet control element 36. The body 35 also defines a slot 40 oriented perpendicular to the pivot axis 34 and a passageway 42 sized to receive the spherical end portion 22. The body 35 defines an array of teeth 46 and outer peripheral surface 44 which is positioned at a constant radius from the pivot axis 34 in a region forward of a stop surface 48. The handle 12 supports a pin 50 that is positioned to engage the body 35 and to resist any tendency of the body 35 to move forwardly in use. The pin 50 also cooperates with the stop surface 48 to limit the maximum counter-clockwise movement of the rod actuator 32.

The ratchet control element 36 is mounted to slide in the bore 38 and is biased outwardly by a spring 52. The ratchet control element 36 supports a finger-contacting surface 54 at its outer or first end 56 (FIGS. 1 and 2). The ratchet control element 36 also includes a ratchet-actuator-contacting portion 58 at its second end and a pawl-contacting portion 62 (FIG. 4). The pawl-contacting portion 62 is arcuate in shape and disposed in the slot 40.

As best shown in FIG. 4, the handle 12 also supports a ratchet mechanism 64 that includes a ratchet pawl 66 coupled to a ratchet actuator 68. In this embodiment the ratchet actuator 68 is formed in one piece with the pawl 66, though this is not required in all embodiments. The pawl 66 and actuator 68 are mounted for pivotal movement with respect to the handle about a shaft 70. This shaft 70 integrally supports eccentric spring studs 72 that extend from both ends of the shaft 70. A set screw (not shown) immobilizes the shaft 70 at the desired rotational position with respect to the handle 12. A pair of extension springs 76 (one on either side of the handle 12) extend between the spring studs 72 and an anchoring shaft 78. These springs 76 bias the pawl 66 and the ratchet actuator 68 in a counter-clockwise direction, such that the pawl 66 is biased toward the teeth 46. The pawl 66 includes a stop surface 80 that limits counter-clockwise motion of the pawl 66. The term "ratchet part" will be used to encompass either portion of a ratchet, such as the pawl 66 or the teeth 46. As shown in FIG. 4, the ratchet actuator 68 is mounted in a distal portion of the handle 12, i.e. closer to the rear than to the front of the handle 12.

Figure 5:
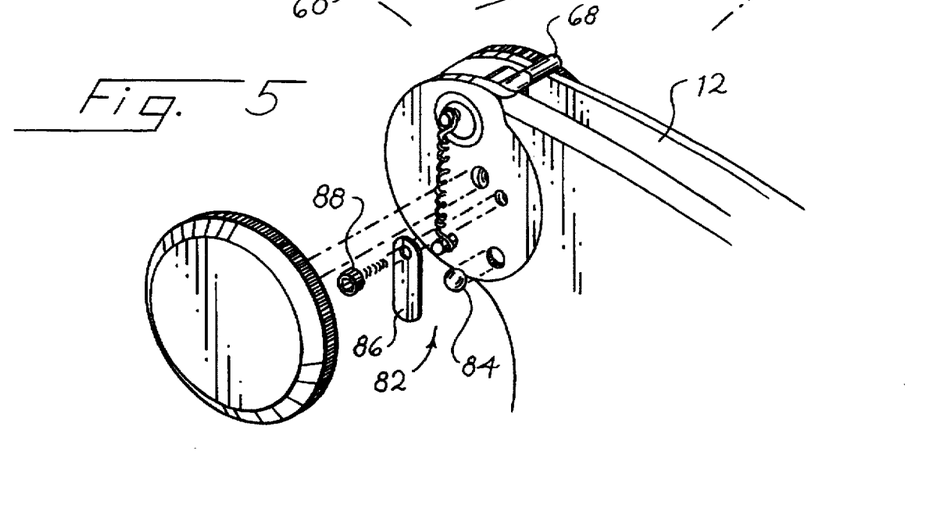
FIG. 5 is an exploded perspective view showing a detent mechanism included in the embodiment of FIGS. 1 and 2.

As best shown in FIG. 5, a detent mechanism 82 is provided to releasably hold the pawl in an off position. The detent mechanism 82 includes identical detent balls 84 on either side of the handle 12. The detent balls 84 are resiliently biased toward the pawl 66 by respective leaf springs 86 that are mounted to the handle 12 by screws 88. When the ratchet actuator 68 is used to move the pawl 66 in a clockwise direction past the balls 84, the balls 84 releasably hold the pawl 66 in an off position, out of engagement with teeth 46 (FIG. 4).

As best shown in FIG. 4, the innermost end of the passageway 42 is preferably shaped with a spherical end mill to define a spherical surface which matches the shape of the spherical end portion 22. Preferably, this spherical end of the passageway 42 is substantially tangent with one edge of the slot 40. The intersection between these two surfaces preferably defines a spherically concave stop surface 90 which matches the shape of the spherical end portion 22. Because the stop surface 90 is spherically concave, it provides area contact between the end portion 22 and the body 35. This arrangement is particularly wear resistant, and it allows the surgical tool 10 to maintain a consistent feel after extensive use.

When the ratchet control element 36 is in the position shown in FIG. 4, the pawl-contacting portion 62 blocks the passageway 42, and prevents the end portion 22 from moving out of the body 35.

Figure 15:
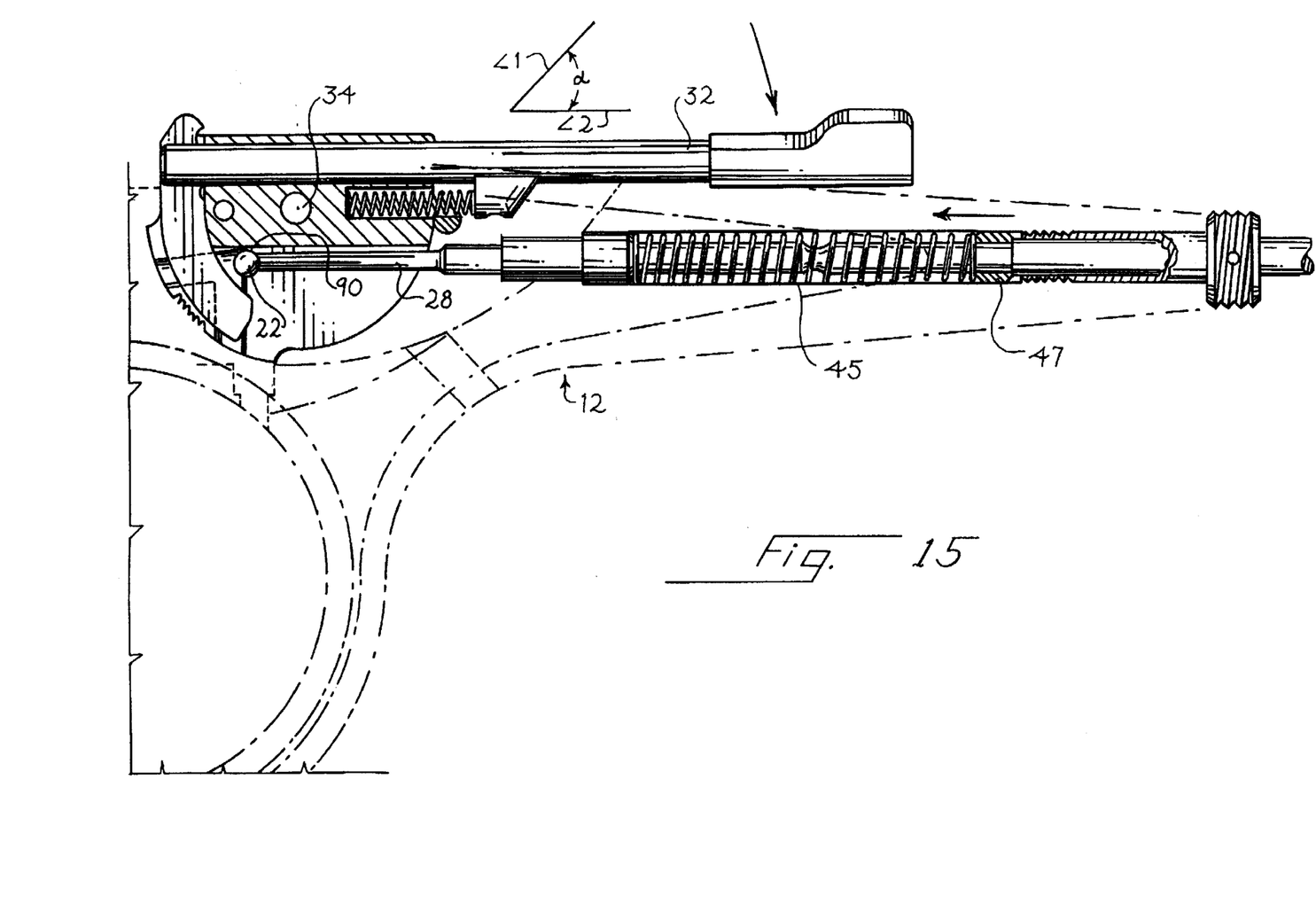
FIG. 15 is a side view in partial cutaway of additional elements of the tool handle of FIGS. 1 and 2.

As best shown in FIG. 15, the handle 12 mounts a compression spring 45 which bears against a slideable spacer ring 47, which in turn bears against a shoulder of the control rod 20, biasing the control rod 20 to the right as shown in FIG. 15. This arrangement ensures that the end portion 22 is always biased into contact with the stop surface 90, thereby eliminating play and providing a positive action between the control rod 20 and the rod actuator 32. Input commands from the user's finger are thereby translated into precisely controlled movements of the movable jaw.

Figure 6:
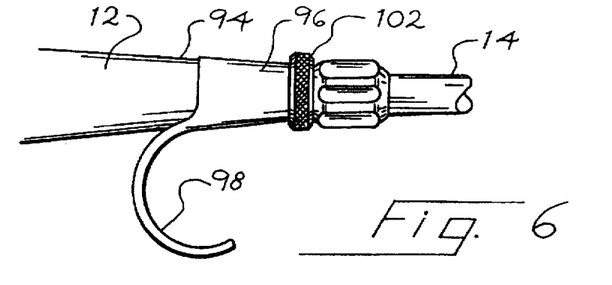
FIGS. 6 and 7 are fragmentary side views showing alternative finger engaging elements suitable for use in the embodiment of FIGS. 1 and 2.
Figure 7:
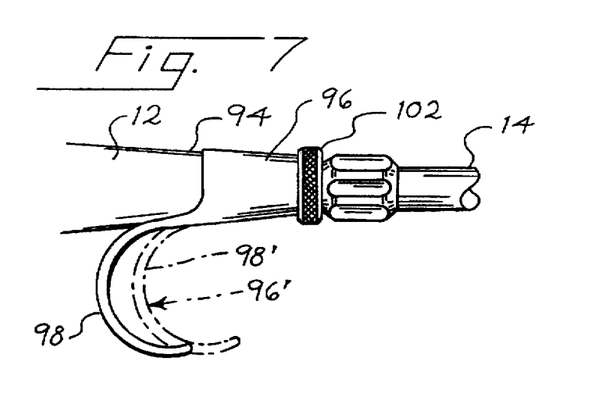
Figure 8:
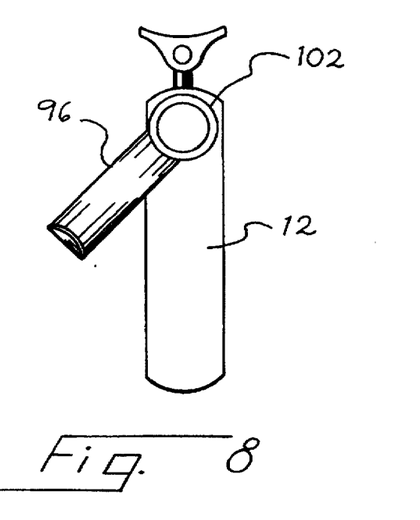
FIGS. 8 and 9 are front views showing alternative rotational positions of the finger engaging element of FIG. 6.
Figure 9:
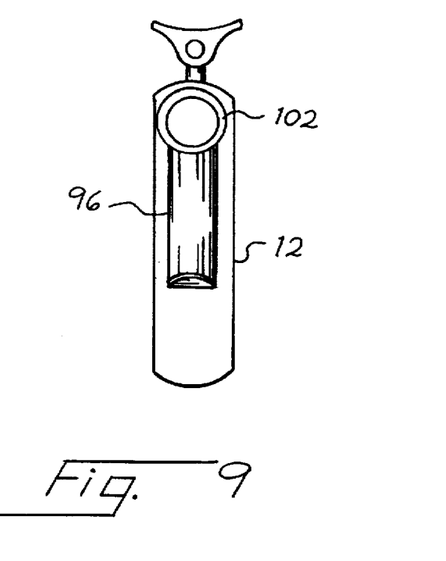

As best shown in FIGS. 6 and 7, the handle 12 defines a conical surface 94 adjacent the shaft 14, and conical surface 94 supports a finger-engaging element 96. The finger-engaging element 96 includes a finger-contacting surface 98, and it defines a conical opening. As shown in FIGS. 8 and 9, the finger-engaging element 96 can be rotated to any desired position with respect to the handle 12. Once in the desired position, it is locked in place with a locking element 102 that is threadedly connected to the handle 12. The finger-engaging element 96 can readily be removed from the handle 12 and replaced with an alternate finger-engaging element 96' that has a differently shaped finger-contacting surface 98' (either larger or smaller, deeper or shallower). See FIG. 7. The conical surface 94 is oriented at an angle β with respect to the centerline of the shaft 14. In this embodiment, β is equal to 5°. β° is preferably less than 9°, and more preferably less than 7°. This arrangement provides a secure lock for the element 96 (or any other element to be adjustably or removably mounted to the handle 12) without the use of a wrench.

Figure 10:
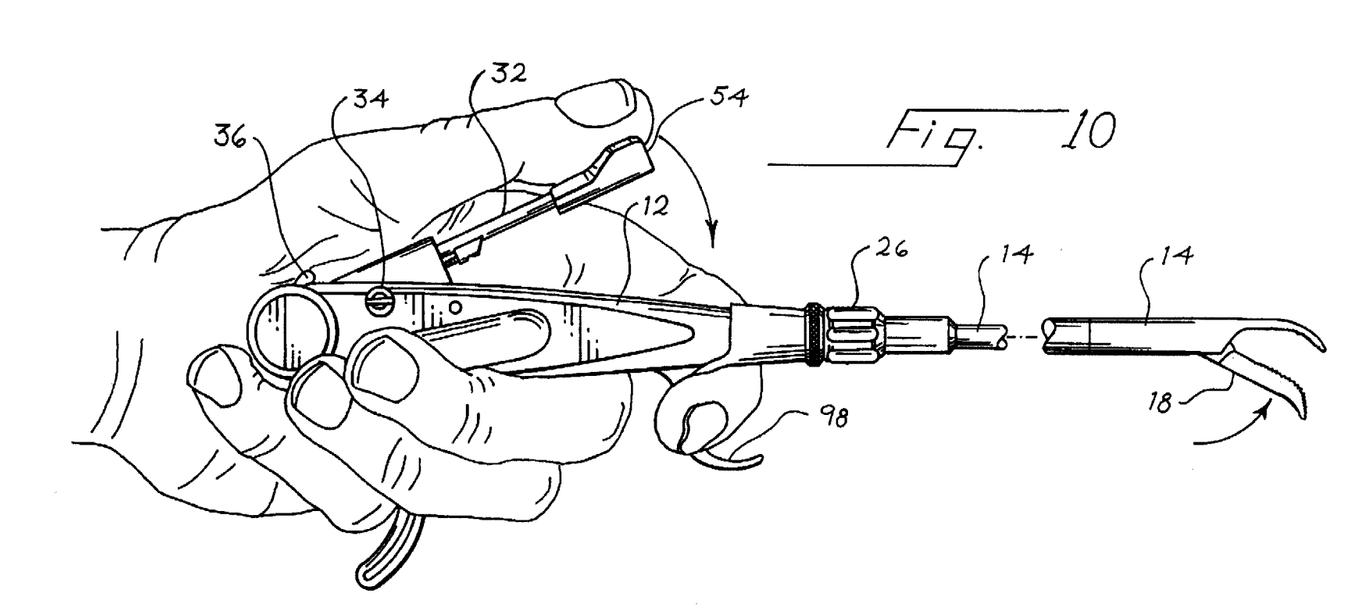
FIG. 10 is a side view showing the embodiment of FIGS. 1 and 2 as held in the hand of a user.

FIG. 10 shows the handle 12 held in the hand of a user. Note that a finger (in this case the thumb) is positioned on the finger-contacting surface 54, and that a second finger is positioned on the finger-contacting surface 98. The ratchet control element 36 is positioned to bear against the palm of the hand of the user. As used herein, the term "finger" is intended broadly to encompass any digit including the thumb, and the term "palm" is intended broadly to include the base of the thumb.

When the handle 12 is held as shown in FIG. 10, the user can readily apply pivoting forces to the rod actuator 32 in order to pivot the rod actuator 32 about the pivot axis 34 and control the position of the movable jaw 18. The user is also well positioned to apply axial forces with the thumb against the end of the finger-contacting surface 54 to perform various control functions as described below.

FIG. 15 shows the handle 12 with the rod actuator 32 pivoted to hold the movable jaw closed. In this position, the end portion 22 is positioned on the opposite side of the pivot axis 34 from the jaws, and the angle α between (1) the line L1 interconnecting the pivot axis 34 and the center of the end portion 22 and (2) a line L2 parallel to the centerline of the rod 28 is about 45°. This arrangement provides the advantage that the mechanical advantage provided by the rod actuator 32 increases as the jaws approach the closed position. This is because the torque arm by which the rod 28 resists pivoting of the rod actuator 32 is proportional to sin α. As the jaws are closed, α is progressively reduced, and the mechanical advantage of the rod actuator 32 is progressively increased. Stated another way, a given angular rotation of the rod actuator 32 produces an increasingly smaller axial movement of the rod 28 (and a corresponding increasingly layer mechanical advantage) as α decreases from 90° toward 0°. The tool 10 is therefore well suited for securely gripping small objects such as suturing needles. In other embodiments the angle α can range between about 30° and 60° when the jaws are in the closed position.

Figure 11:
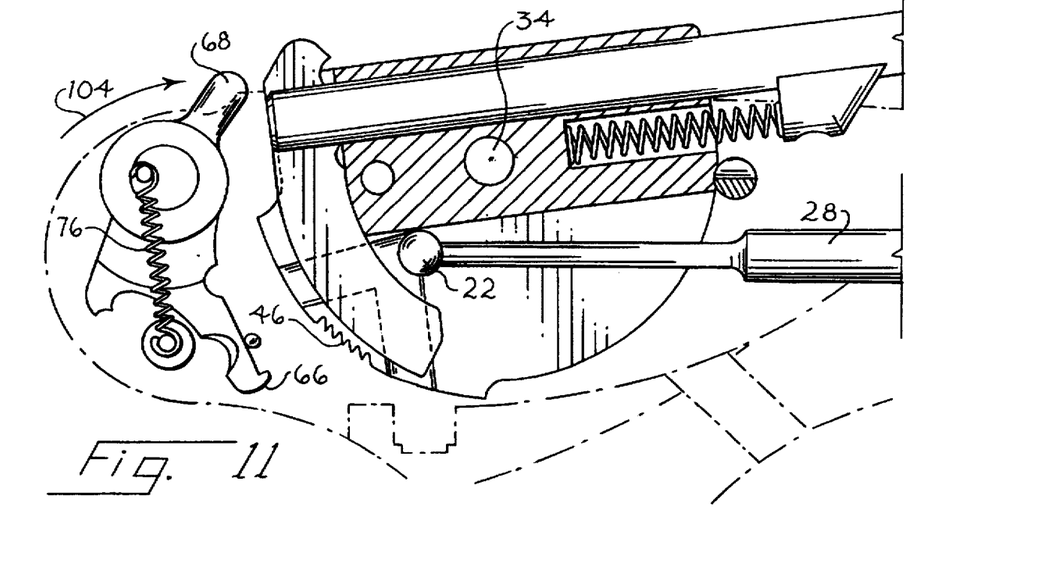
FIG. 11 is a fragmentary sectional view showing the manner in which forces can be applied with the palm of the user to release the pawl.

FIG. 11 shows a first mode of operation in which the user applies axial forces to the finger-engaging element in order to push the ratchet actuator 68 against the palm of the user. The palm thereby applies forces in the direction of the arrow 104 to move the pawl 66 against the force of the springs 76, out of engagement with the teeth 46.

In FIG. 11, sufficient forces have been applied to the ratchet actuator 68 with the palm of the user to move the pawl 66 to the ratchet off position. Alternately, smaller forces in the direction of the arrow 104 may be applied to release the pawl 66 from the teeth without engaging the detent.

Figure 12:
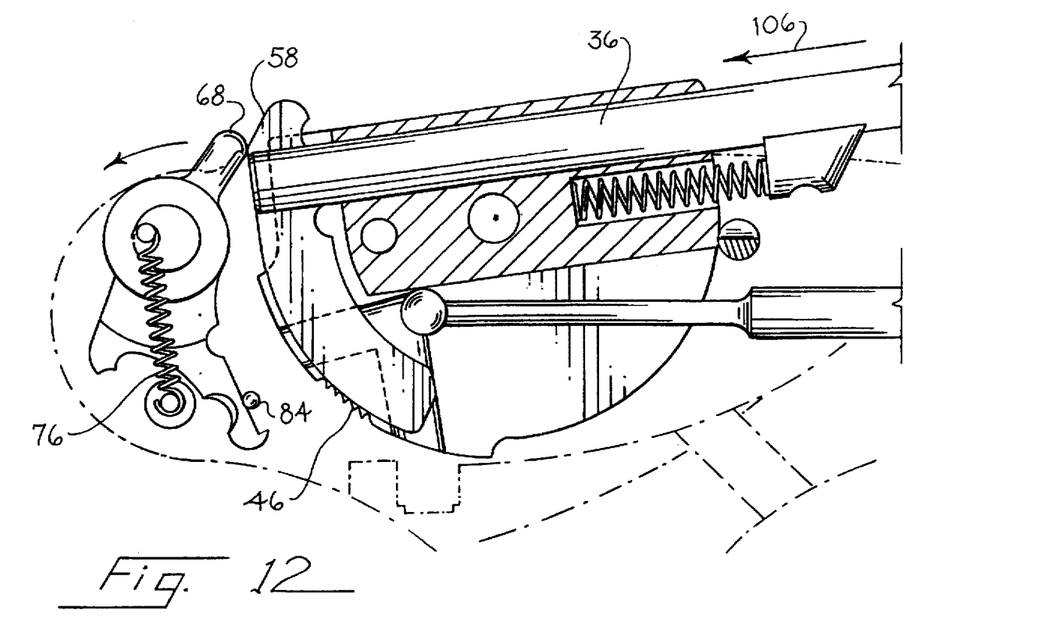
FIG. 12 is a view corresponding to FIG. 11 showing the manner in which the user can apply axial forces to move the pawl away from an off position.

FIG. 12 shows another mode of operation in which the user has applied axial forces in the direction of the arrow 106 to bring the ratchet actuator contacting portion 58 into contact with the ratchet actuator 68, and thereby to urge the pawl 66 past the detent balls 84 to a point where the springs 76 again bias the pawl 66 against the teeth 46.

Figure 13:
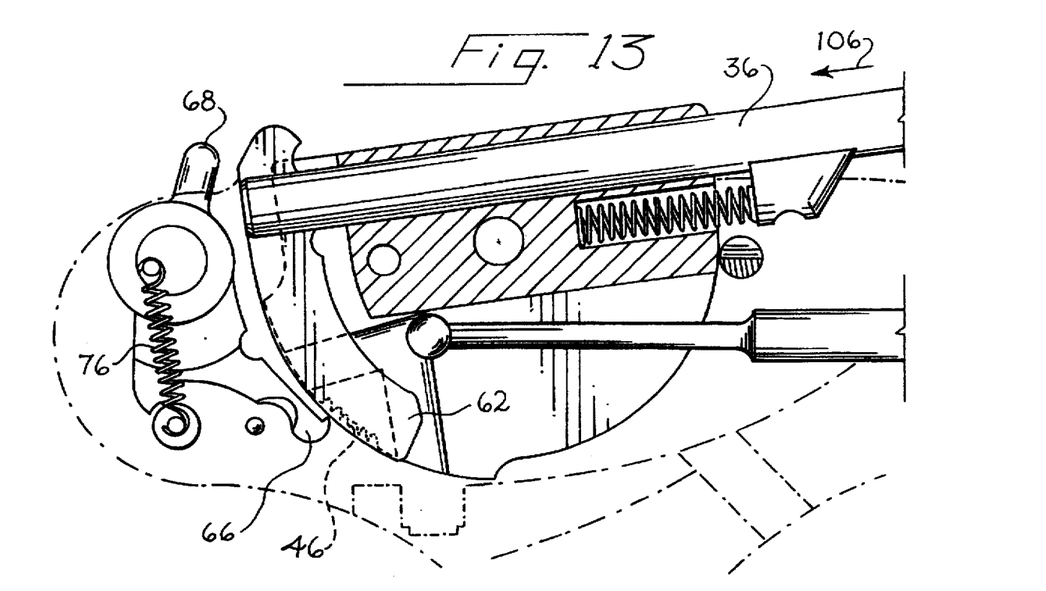
FIG. 13 is a view corresponding to FIG. 11 showing the manner in which a user can apply axial forces to momentarily release the pawl.

FIG. 13 shows a third mode of operation, in which the user has applied axial forces to move the ratchet control element 36 to bring the pawl-contacting portion 62 into contact with the pawl 66 and thereby to release the pawl 66 from engagement with the teeth 46.

Figure 14:
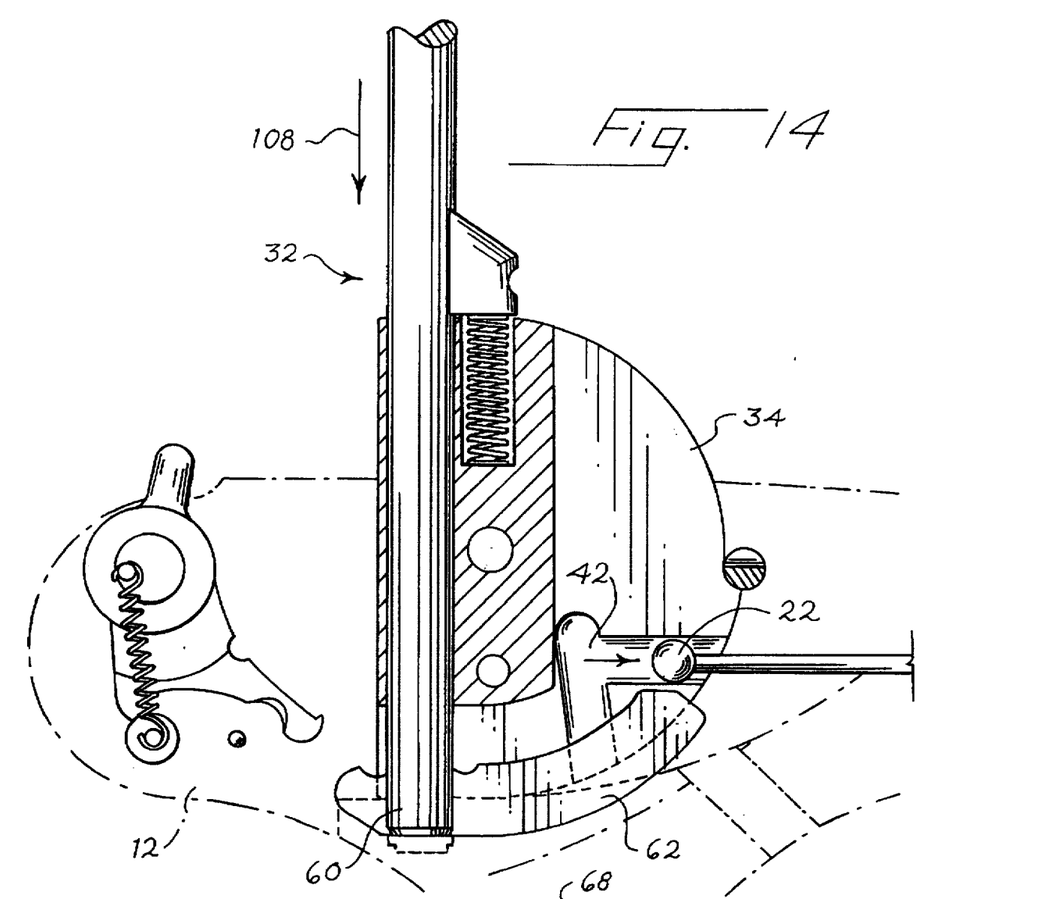
FIG. 14 is a view corresponding to FIG. 11 showing the manner in which the user can apply axial forces to lock the actuator in position for insertion and removal of a control rod.

FIG. 14 shows another mode of operation in which the user has unthreaded the barrel, rotated the rod actuator 32 in the counter-clockwise direction, and then applied axial forces in the direction of the arrow 108 to move the second end 60 into a recess formed in the handle 12. In this position the second end 60 immobilizes the rod actuator 32 in a predetermined pivotal position. Simultaneously, the passageway 42 is opened, and the end portion 22 is therefore free to move via the passageway 42 into and out of the body 35. In this way the shaft and associated elements including the control rod 20 can readily be removed from or installed onto the handle 12.

The preferred embodiment described above provides a number of important advantages. First, the design is an ergonomic design which can easily be used, and which does not require the user to shift his or her grip on the handle in order to perform all control functions during normal operation. The handle 12 is symmetrical from right to left, and is therefore suitable for use with either hand. The handle 12 can readily be adjusted by altering the rotational position or size of the finger-engaging element 96.

Because of the arrangement of the ratchet control element, the ratchet actuator and the pawl, the user can readily release the ratchet mechanism without an abrupt discharge of energy. This can be done by biasing the rod actuator in a clockwise direction about the pivot axis 34 in order to remove strain on the ratchet mechanism, and then disengaging the ratchet mechanism using any of the techniques described above. This allows reduced movement of the jaws 16, 18 when the ratchet mechanism is disengaged, which can be an important operational advantage.

Because the shaft 14 is removably mounted on the handle 12, the shaft 14 and the attached jaws 16, 18 can readily be exchanged when necessary. The handle 12 has been designed to be long wearing and easily calibratable. In particular, the arrangement discussed above allows the length of the control rod 20 to be calibrated readily, and ensures that a predictable feel is obtained as alternative shafts 14 are installed on the handle 12. The area contact provided by the stop surface 90 and the wear resistance provided by the pin 50 reduce the tendency of the handle 12 to change in critical dimensions during use.

Of course, it should be understood that a wide range of changes and modifications can be made to the preferred embodiment described above. Proportions, configurations and shapes can all be adapted as appropriate for the particular application. The various features described above can be used independently, rather than in combination. It is therefore intended that the foregoing detailed description be regarded as an illustration of selected forms that the invention can take and not as a limitation of the invention. It is only the following claims, including all equivalents, that are intended to define the scope of this invention.

I claim:

1. In a surgical tool of the type comprising a shaft, a movable element mounted to the shaft, a handle mounted to the shaft, and a control rod coupled to the movable element and extending into the handle, the improvement comprising:
    a rod actuator mounted in the handle to pivot about a pivot axis and coupled to the control rod such that pivoting movement of the rod actuator with respect to the handle causes the control rod to translate with respect to the shaft;
    a ratchet part mounted in the handle and coupled to the rod actuator; and
    a ratchet actuator coupled to the ratchet part and mounted in a distal part of the handle such that the pivot axis is disposed intermediate the ratchet actuator and the shaft, said ratchet actuator operating to selectively decouple the ratchet part from the actuator, said ratchet actuator positioned to contact a palm of a user when the user grasps the handle and places a finger on the rod actuator.

2. The invention of claim 1 further comprising a detent mechanism mounted in the handle to releasably hold the ratchet part in an off position, out of engagement with the rod actuator, wherein said ratchet actuator is operative to move the ratchet part to the off position when the user presses the palm against the ratchet actuator with adequate force.

3. The invention of claim 1 wherein the rod actuator comprises a body and a ratchet control element, said ratchet control element movably mounted with respect to the body and comprising a finger-contacting portion and a ratchet-actuator-contacting portion, said finger-contacting portion positioned to contact the finger of the user to accept both pivoting forces tending to pivot the rod actuator in the handle and axial forces tending to move the ratchet control element in the body, said ratchet-actuator-contacting portion positioned to contact the ratchet actuator to move the ratchet part toward the actuator body when axial forces are applied to the ratchet control element.

4. The invention of claim 3 wherein the ratchet control element further comprises a ratchet-part-contacting-portion positioned to contact the ratchet part to move the ratchet part away from the actuator body when axial forces are applied to the ratchet control element.

5. The invention of claim 1 wherein the rod actuator comprises a body and a ratchet control element, said ratchet control element movably mounted with respect to the body and comprising a finger-contacting portion and a ratchetpart-contacting portion, said finger-contacting portion positioned to contact the finger of the user to accept both pivoting forces tending to pivot the rod actuator in the handle and axial forces tending to move the ratchet control element in the body, said ratchet part-contacting portion positioned to contact the ratchet part to move the ratchet part away from the actuator body when axial forces are applied to the ratchet control element.

6. The invention of claim 1 wherein the rod actuator comprises a body and an element movably mounted in the body, said element comprising a first end and a second end, said first end positioned to contact the finger of the user to accept both pivoting forces tending to pivot the rod actuator in the handle and axial forces tending to move the element in the body; and wherein said handle forms a recess sized to receive the second end when the element is aligned with the recess and axial forces are applied to the first end; said second end operating to lock the rod actuator in the housing at a selected pivotal orientation to facilitate installation of the control rod in the body.

7. In a surgical tool of the type comprising a shaft, a movable element mounted to the shaft, a handle mounted to the shaft, and a control rod coupled to the movable element and extending into the handle, the improvement comprising:

a rod actuator mounted in the handle to pivot about a pivot axis and coupled to the control rod such that pivoting movement of the rod actuator with respect to the handle causes the control rod to translate with respect to the shaft; and a ratchet part mounted in the handle and coupled to the rod actuator;

wherein the rod actuator comprises a body and a ratchet control element, said ratchet control element slidably mounted with respect to the body and comprising a finger-contacting portion and a ratchet-part-contacting portion, said finger-contacting portion positioned to contact a finger of a user to accept both pivoting forces tending to pivot the rod actuator in the handle and axial forces tending to slide the ratchet control element in the body, said ratchet-part-contacting portion positioned to contact the ratchet part to move the ratchet part away from the actuator body when axial forces are applied to the ratchet control element.

8. In a surgical tool of the type comprising a shaft, a movable element mounted to the shaft, a handle mounted to the shaft, and a control rod coupled to the movable element and extending into the handle, the improvement comprising:

a rod actuator mounted in the handle to pivot about a pivot axis and coupled to the control rod such that pivoting movement of the rod actuator with respect to the handle causes the control rod to translate with respect to the shaft; and a ratchet part mounted in the handle and coupled to the rod actuator; and wherein the rod actuator comprises a body and an element movably mounted in the body, said element comprising a first end and a second end, said first end positioned to contact the finger of the user to accept both pivoting forces tending to pivot the rod actuator in the handle and axial forces tending to move the element in the body; and wherein said handle forms a recess sized to receive the second end when the element is aligned with the recess and axial forces are applied to the first end; said second end operating to lock the rod actuator in the housing at a selected pivotal orientation to facilitate installation of the control rod in the body.

9. In a surgical tool of the type comprising a shaft, a movable element mounted to the shaft, a handle mounted to the shaft, and a control rod coupled to the movable element and extending into the handle, the improvement comprising:

a rod actuator mounted in the handle to pivot about a pivot axis and coupled to the control rod such that pivoting movement of the rod actuator with respect to the handle causes the control rod to translate with respect to the shaft;

a finger-engaging element removably mounted to the handle adjacent the shaft, said finger-engaging element rotatable with respect to the handle to a plurality of positions distributed around the shaft; and a locking element coupled to the handle to lock the finger-engaging element in a selected one of the positions.

10. The invention of claim 9 wherein the finger-engaging element comprises a curved finger-contacting surface facing the shaft.

11. The invention of claim 9 wherein the handle comprises a conical surface adjacent the shaft, and wherein the finger-engaging element forms a conical opening shaped to receive the conical surface.

12. In a surgical tool of the type comprising a shaft, a movable element mounted to the shaft, a handle mounted to the shaft, and a control rod coupled to the movable element and extending into the handle, the improvement comprising:

a rod actuator mounted in the handle to pivot about a pivot axis and coupled to the control rod such that pivoting movement of the actuator with respect to the handle causes the control rod to translate with respect to the shaft;

said control rod comprising a spherical end portion;

said rod actuator comprising a slot oriented in a plane transverse to the pivot axis and a passageway that intersects the slot, said rod actuator comprising a stop surface adjacent the slot and shaft;

a portion of said control rod disposed in the slot, said spherical end portion disposed in the passageway and reacting against the stop surface.

13. The invention of claim 12 wherein the stop surface is spherically concave to provide area contact between the spherical end portion and the rod actuator.

14. In a surgical tool of the type comprising a shaft, a movable element mounted to the shaft, a handle mounted to the shaft, and a control rod coupled to the movable element and extending into the handle, said control rod comprising an end portion, the improvement comprising:

a rod actuator mounted in the handle to pivot about a pivot axis and coupled to the control rod such that pivoting movement of the actuator with respect to the handle causes the control rod to translate with respect to the shaft;

said end portion and said movable element positioned on opposite sides of the pivot axis when the movable element is in a closed position;

said rod actuator comprising an angle α between (1) a line between the pivot axis and a central point of the end portion and (2) a center line of the control rod;

said angle α being in the range 30°–60° when the movable element is in the closed position.

15. The invention of claim 14 wherein the angle α is substantially equal to 45° when the movable element is in the closed position.

16. In a surgical tool of the type comprising a shaft, a movable element mounted to the shaft, a handle mounted to the shaft, and a control rod coupled to the movable element, comprising an end portion, and extending into the handle, the improvement comprising:

- a rod actuator mounted in the handle to pivot about a pivot axis and coupled to the control rod such that pivoting movement of the actuator with respect to the handle causes the control rod to translate with respect to the shaft;
- a spring coupled between the handle and the rod to bias the end portion against the rod actuator, and thereby to reduce play therebetween.

17. The invention of claim 16 further comprising:

- a ratchet part mounted in the handle and coupled to the rod actuator; and
- a ratchet actuator coupled to the ratchet part and mounted in a distal part of the handle such that the pivot axis is disposed intermediate the ratchet actuator and the shaft, said ratchet actuator operating to selectively decouple the ratchet part from the actuator, said ratchet actuator positioned to contact a palm of a user when the user grasps the handle and places a finger on the rod actuator.

18. The invention of claim 16 further comprising:

- a ratchet part mounted in the handle and coupled to the rod actuator;
- wherein the rod actuator comprises a body and a ratchet control element, said ratchet control element slidably mounted with respect to the body and comprising a finger-contacting portion and a ratchet-part-contacting portion, said finger-contacting portion positioned to contact a finger of a user to accept both pivoting forces tending to pivot the rod actuator in the handle and axial forces tending to slide the ratchet control element in the body, said ratchet-part-contacting portion positioned to contact the ratchet part to move the ratchet part away from the actuator body when axial forces are applied to the ratchet control element.

19. The invention of claim 16 wherein said rod actuator comprises a slot oriented in a plane transverse to the pivot axis and a passageway that intersects the slot, said rod actuator comprises a stop surface adjacent the slot and shaft;

a portion of said control rod is disposed in the slot, said spherical end portion is disposed in the passageway and reacts against the stop surface.

20. The invention of claim 16 wherein said rod actuator comprises an angle $\alpha$ between (1) a line between the pivot axis and a central point of the end portion and (2) a center line of the control rod;

said angle $\alpha$ being in the range 30°–60° when the movable element is in the closed position.

21. In a surgical tool of the type comprising a shaft, a movable element mounted to the shaft, a handle mounted to the shaft, and a control rod coupled to the movable element and extending into the handle, the improvement comprising:

said handle comprising a mounting surface positioned adjacent the shaft, said mounting surface being shaped as a portion of a cone and defining an angle $\beta$ between the mounting surface and a centerline of the shaft; $\beta$ having a value less than 9°.

22. The invention of claim 21 wherein $\beta$ is less than 7°.

23. The invention of claim 21 wherein $\beta$ is about equal to 5°.

24. The invention of claim 21 further comprising:

- a rod actuator mounted in the handle to pivot about a pivot axis and coupled to the control rod such that pivoting movement of the rod actuator with respect to the handle causes the control rod to translate with respect to the shaft;
- a finger-engaging element removably mounted to the mounting surface adjacent the shaft, said finger-engaging element rotatable with respect to the handle to a plurality of positions distributed around the shaft; and
- a locking element coupled to the handle to lock the finger-engaging element in a selected one of the positions.

* * * * *